(12) United States Patent
Telles et al.

(10) Patent No.: US 6,794,129 B1
(45) Date of Patent: Sep. 21, 2004

(54) METHOD FOR MEASURING ANTI-PROTEASE RESISTANCE OF HIV-2 IN A PATIENT

(75) Inventors: Jean-Noel Telles, Paris (FR); Francoise Brun-Vezinet, Paris (FR); Diane Descamps, Paris (FR)

(73) Assignees: Bio Merieux, Marcy-l'Etoile (FR); Assistance Publique-Hopitaux de Paris, Paris (FR)

( * ) Notice: Subject to any disclaimer, the term of this patent is extended or adjusted under 35 U.S.C. 154(b) by 0 days.

(21) Appl. No.: 09/980,777
(22) PCT Filed: Jun. 21, 2000
(86) PCT No.: PCT/FR00/01728
 § 371 (c)(1),
 (2), (4) Date: Feb. 20, 2002
(87) PCT Pub. No.: WO00/78990
 PCT Pub. Date: Dec. 28, 2000

(30) Foreign Application Priority Data

Jun. 21, 1999 (FR) .............................. 99/07855

(51) Int. Cl.⁷ ................................. C12Q 1/70
(52) U.S. Cl. ............................ 435/5; 435/7.1; 435/7.4; 435/23; 435/24; 536/23.72
(58) Field of Search ............................ 435/5, 7.1, 7.4, 435/23, 24; 536/27.72

(56) References Cited

U.S. PATENT DOCUMENTS 5,436,131 A 7/1995 Condra et al.

FOREIGN PATENT DOCUMENTS

| WO | WO 90 14842 A | 12/1990 |
| WO | WO 96 08580 A | 3/1996 |
| WO | WO 99 38961 A | 8/1999 |
| WO | WO 99 67428 A | 12/1999 |

OTHER PUBLICATIONS

Melnick et al., "An Escherichia coli expression assay and-screen for immunodeficiency virus protease variants with decreased susceptibility to indinavir", Antimicrobial agents and Chemotherapy, vol. 42, No. 12, 1998, pp. 3256–3265.

Vasudevachari et al., "Emergence of protease inhibitor resistance mutations in human immunodeficiency virus type 1 isolates from patients and rapid screening procedure for their detection" Antimicrobial Agents and Chemotherapy vol. 40, No. 11, 1996, pp 2535–2541.

Maschera et al, "Analysis of resistance to human immunodeficiency virus type 1 protease inhibitors by using matched bacterial expression and proviral infection vectors" Journal of Virology vol. 69, No. 9, 1995, pp. 5431–5436.

Martinez–Picado et al., "Replicative fitness of protease inhibitor–resistant mutant of human immunodeficiency virus type 1" Journal of Virology, US, The American Society For Microbiology, vol. 73, No. 5, May 1999 (May 1999), pp. 3744–3752.

*Primary Examiner*—Jeffrey Stucker
(74) *Attorney, Agent, or Firm*—Oliff & Berridge PLC

(57) ABSTRACT

A search method in a biological sample containing an HIV 2 viral strain for possible resistance of said strain to treatment by an anti-protease agent, and nucleotide probes for the implementation thereof. According to methods known per se, the presence of at least one mutation at certain, specified, particular positions of the proteinic sequence of the protease of said viral strain from a biological sample taken from a patient contaminated by HIV 2 is searched. If said mutation is observed, the existence of a resistance to said anti-protease agent is assumed in the patient.

22 Claims, No Drawings

METHOD FOR MEASURING ANTI-PROTEASE RESISTANCE OF HIV-2 IN A PATIENT

BACKGROUND OF THE INVENTION

1. Field of Invention

The invention relates to a method for testing the resistance of the HIV-2virus to antiprotease treatment in a patient infected with HIV-2 as well as nucleotide probes usable for such testing.

2. Description of Related Art

Acquired immunodeficiency syndrome (AIDS) is caused by two viruses: HIV-1 and HIV-2. HIV-1 is present throughout the world while HIV-2 is present mainly in western Africa.

Effective antiviral treatments have been in widespread use since 1996 in developed countries where the virus present is HIV-1. Because of their cost, these treatments cannot be used in developing countries where HIV-2 is present.

There are three types of antiretroviral treatments: antiprotease (Indinavir, Ritonavir, Saquinavir, Nelfinavir, and Amprenavir), nucleoside reverse transcriptase (RT) inhibitors (Zidovudine, Didanosine, Zalcitabine, Lamivudine, Stavudine, Abacavir, FTC, and Adefovir), and nonnucleoside RT inhibitors (Nevirapine, Delavirdine, and Efavirenz). These treatments are often given in combination; this is known as multiple-drug therapy.

Antiproteases elicit primary mutations which confer a high degree of resistance but alter the ability of the virus to replicate. Thus, the virus needs to select secondary mutations if it is to be both resistant and able to replicate actively. Also, reverse transcriptase mutations have been described where nucleoside RT inhibitors have been used in combination.

During treatment with HIV-1 infection, particularly if the levels of drug in the bloodstream are inadequate, viral replication is insufficiently inhibited, or rises above the detection threshold of available viral load techniques (the "viral load" measures the quantity of virus genomes in the bloodstream). Because of the high error rate of reverse transcription, mutations take place in the genes targeted by protease and reverse transcriptase treatment. Certain mutations bring about various degrees of resistance to antivirals. Virologic failure occurs in 20 to 40% of patients treated with current multiple drug regimens.

If viruses resistant to one or more substances can be shown for a patient before treatment or if the viral load increases again, the best drug combination for treating HIV-1 can be chosen.

There are currently no published data on mutations in the HIV-2 genome due to the use of antiproteases.

Antiprotease agents that are active against HIV-1 are also active against HIV-2. However, there are no methods available to assist the clinician in determining resistance to antiprotease drugs in patients infected with HIV-2.

SUMMARY OF THE INVENTION

The amino acid sequence of the HIV-2 protease is known. In the present application, the numbering system for this amino acid sequence can be deduced from that described in Human Retroviruses and Aids, 1997, Los Alamos National Laboratory, Los Alamos, N.Mex., Chapter II, pp. B10 and B11. The first amino acid in the protease sequence, considered to be position 1 in the present application, is the proline in position 86 of the polyprotein PoL in the ROD strain.

It has now been discovered that antiprotease drugs can bring about mutations in positions 45, 54, 64, 84, and 90 and in positions 10, 46 of the HIV-2 protease and that the mutated viral strains thus appearing are usually resistant to at least one of the antiprotease drugs used.

Hence, the subject of the present invention is a method for testing resistance of an HIV-2 viral strain to antiprotease treatment.

In a preliminary testing phase, this is a method wherein:
a) using known methods, the presence of at least one mutation at one of positions 45, 54, 64, 84, and 90 or one of positions 10, 46 of the protein sequence of the protease of said viral strain in a biological sample taken from a patient infected with HIV-2 is investigated,
b) of the mutations founds in a), those which, after cloning in an HIV-2 virus, do not prevent the virus clone obtained from multiplying in culture in the presence of said antiprotease drug are selected, and
c) if at least one mutation is selected at step b), it is concluded that resistance exists to the antiprotease drug referred to in b).

Of the mutations found in a), those which, when present in a gene cloned in an HIV-2 virus, cause the viral clone not to be significantly prevented from multiplying in the presence of said antiprotease drug are selected. The following procedure may be used to implement step b). The mutations tested are inserted individually into a viral clone by mutagenesis directed by the method described in the article by Kemp et al., J. Virol., 72(6), pp. 5093–5098, 1998. The clones thus obtained are cultured with a "wild-type" (i.e. non-mutated) virus clone as a reference in the presence of the various antiprotease drugs able to act against the HIV-2 virus. By measuring the $IC_{50}$ with a colorimetric test for example (see above Kemp article), the size of the mutation (minor or major) with the various drugs tested can be determined. Thus, one can select the mutations that allow the virus to multiply in the presence of an antiprotease agent as these mutations give rise to strains resistant to this antiprotease.

Of course, in the case outlined in c), the future treatment planned for the patient would be a different antiprotease agent from the agent shown to elicit resistance in this patient.

If step b) did not select a mutation found in step a), it may be concluded that the mutation in question did not elicit resistance by the HIV-2 virus to the antiprotease drug tested for the patient in question.

Obviously, when step b) identifies a mutation that generates resistance to a given antiprotease drug, step b) of the method described above need not be carried out in the future. In this case, step a) would suffice because the link between the mutation and resistance to the antiprotease drug would be established once and for all; one can go on directly to step c) and conclude that there is resistance to the antiprotease agent studied.

The invention relates in particular to a method for detecting any resistance of an HIV-2 viral strain to treatment by an antiprotease drug in which the presence of at least one mutation chosen from the following mutations:

K45R, I54M, I64V, I84L and L90M, or V10I, I46V, and I82M, in the protein sequence of the protease of said viral strain is investigated and in which said resistance is concluded to exist if said mutation or said mutations is or are present.

The conventional notation in the present application for describing a mutation is as follows: The number indicates the position in the amino acid sequence of the HIV-2 protease. The letter to the left of the number is the amino acid of the wild-type strain in the international classification, with the one-letter code. The letter to the right of the number is the amino acid, in the same classification, resulting from a mutation.

"Wild-type strain" is understood to be a viral strain that has not mutated after treatment with an antiprotease.

To identify a mutation in the protein sequence of the protease of the viral strain in question, it is preferable to look for a corresponding mutation in the nucleotide sequence of the gene of said protease. These mutations can be tested on the DNA or the RNA. Of course, in looking for a mutation in the protein sequence by seeking a mutation in the nucleotide sequence, degeneration of the genetic code would be taken into account, namely a given amino acid can be coded by different codons. This mutation assay can be done in the nucleotide sequence by known methods, particularly by hybridization or sequencing techniques.

DETAILED DESCRIPTION OF PREFERRED EMBODIMENTS

In a first embodiment of the invention, a hybridization method using specific probes is implemented to test for the mutation or mutations.

A particular embodiment using a hybridization method consists of obtaining a polynucleotide containing all or part of the protease gene, and including the sequence of interest corresponding to the region containing the mutation to be assayed. Such a polynucleotide can be obtained in particular by enzymatic amplification. The method used in this case comprises the steps consisting of placing said polynucleotide in contact with a nucleotide probe that is attached or attachable to a solid substrate and is able to hybridize specifically with such a polynucleotide only if the polynucleotide has the mutation studied; then revealing the presence of the polynucleotide attached to the solid substrate by the capture probe, using known methods. For this purpose, the solid substrate can be washed, after which the presence of the polynucleotide, attached to the substrate, is revealed either by a physical method or with an appropriate marker.

The probe can be attached directly by adsorption or by covalence. It can also be attached indirectly by a ligand/antiligand-type reaction such as the biotin/streptavidin or haptene/antibody pair, with the antiligand attaching to the solid substrate and the ligand to the probe, for example.

The polynucleotide can also be labeled during the enzymatic amplification stage, for example using a triphosphate nucleoside labeled for the amplification reaction. The labeled nucleotide will be a deoxyribonucleotide in amplification systems generating a DNA, such as PCR, or a ribonticleotide in amplification techniques generating an RNA, such as the TMA or NASBA techniques.

The polynucleotide can also be labeled after the amplification stage, for example by hybridizing a probe labeled by the sandwich hybridizing technique described in document WO 91/19812.

A particular method of labeling polynucleotides is described in application FR 98 07870 by the applicant.

Alternatively, the polynucleotide including all or part of the protease gene can be prepared by enzymatic amplification, elongating primers that have a ligand. The polynucleotide obtained, which will thus contain the ligand, can be attached to the solid substrate by interaction with a corresponding antiligand. The solid substrate to which the polynucleotide is attached is then placed in contact with at least one probe able to attach specifically to the polynucleotide only if it contains the sought-after mutation. If this mutation is present, the probe will be attached to the solid substrate by the hybrid it forms with the polynucleotide, which itself is attached. One need then only reveal the presence of the hybrid so formed by known methods.

In another embodiment, a hybridization method is used that comprises the steps of enzymatically amplifying ail or part of the protease gene using primers carrying a ligand to generate a polynucleotide having at least one ligand, attaching the polynucleotide to a solid substrate by interaction with an antiligand as described above, placing said attached polynucleotide in contact with at least one probe capable of hybridizing specifically therewith, and revealing the hybrid formed, if any. The probe must hybridize only if the polynucleotide contains the sought-after mutation.

Other detection methods by hybridization may be considered such as that described in Kricka et al., Clinical Chemistry, 45(4), pp. 453–458, 1999 or Keller G. H. et al., DNA Probes, 2nd Ed., Stockton Press, 1993, sections 5 and 6, pp. 173–249.

The "solid substrate" as used here includes all the materials on which a polynucleotide can be immobilized. Synthetic materials or natural materials, that may be chemically modified, can be used for the solid substrate, particularly polysaccharides such as cellulose-based materials, for example paper, cellulose derivatives such as cellulose acetate and nitrocellulose, or dextran; polymers, copolymers, particularly those based on styrene-type monomers, natural fibers such as cotton, and synthetic fibers such as nylon; minerals such as silica, quartz, glasses, and ceramics; latexes; magnetic particles; metal derivatives; gels; etc. The solid substrate may be in the form of a microtitration plate, a membrane as described in application WO 9412670, a particle, or a biochip.

"Biochip" is understood to be a solid substrate of small size to which a plurality of polynucleotides are attached at predetermined positions.

Examples of these biochips are given for example in the publications of G. Ramsay, Nature Biotechnology, 16, pp. 40–44, 1998; F. Ginot, Human Mutation, 10, pp. 1–10, 1997; J. Cheng et al., Molecular Diagnosis, 1(3), pp. 183–200, 1996; T. Livache et al., Nucleic Acids Research, 22(15), pp. 2915–2921, 1994; J. Cheng et al., Nature Biotechnology, 16, pp. 541–546, 1998. The main property of the solid substrate must be to preserve the hybridization properties of the probes on the target and allow a minimum background noise for the detection method. One advantage of biochips is that they simplify the use of numerous probes, taking into account the polymorphism of the virus in areas abutting the sought-after mutation. A biochip for verifying the presence or absence of mutations can be made by the procedure described by Kozal M. et al., Nature Medicine, 2, pp. 753–759, 1996, as a function of alignments of sequences known for different HIV-2 strains.

A "marker" is understood to be a tracer able to generate a signal. A nonexhaustive list of these tracers includes enzymes producing a detectable signal, for example by colorimetry, fluorescence, or luminescence, such as horseradish peroxidase, alkaline phosphatase, beta-galactosidase, glucose-6-phosphate-dehydrogenase; chromophores such as fluorescent, luminescent, or dye compounds; electron density groups detectable by electron microscopy, or by their electrical properties such as conductivity, by amperometry or voltametry methods, or by impedance measurement; groups detectable by optical methods such as diffraction, surface plasmon resonance, or variation in contact angle, or by physical methods such as atomic force spectroscopy, tunnel effect, etc.; radioactive molecules such as $^{32}$P, $^{35}$S, or $^{125}$I.

Signal amplification systems can be used as described in document WO/95 08000 and in this case, the preliminary enzymatic amplification reaction may be unnecessary.

The term "primer" designates an oligonucleotide sequence able to hybridize to a useful nucleic sequence and to serve as a starting point for an enzymatic elongation reaction to produce a nucleic acid fragment complementing a target of interest such as the gene of the protease or part of this gene. The primer has a size of between 5 and 50 nucleotides, particularly between 10 and 30 nucleotides. Preferably, the primers are chosen in the preserved regions of the HIV-2 virus to enable all the viral strains that could be encountered in a patient to be amplified in order to deal with the polymorphism inherent in the HIV-2 virus.

The probes for demonstrating mutations at positions 45 and/or 54 and/or 64 and/or 84 and/or 90, as well as those showing mutations at positions 10 and/or 46 by hybridizing on all or part of the protease gene of the HIV-2 virus present in a biological sample, are also a subject of the present invention.

The term "probe" refers to an oligonucleotide sequence able to hybridize specifically with a nucleic acid sequence of interest. Here, since the goal of the present invention is to detect a point mutation on the gene of the HIV-2 protease, the probe must be able to distinguish a point mutation under predetermined hybridization or washing conditions. The size of these probes is between 5 and 40 nucleotides, particularly between 9 and 25 nucleotides. Methods for determining these probes have been described for example in the patent application WO 97/27332. The probe is, for example, constructed such that the position of the mutation to be detected is substantially in the center of the probe.

The oligonucleotides used as primers or probes can include natural or modified nucleotides such as phosphorothioates, H-phosphonates, alkylphosphorothioates, or analogs of nucleotides containing bases such as inosine or nebularin in the place of the purine or pyrimidine bases present in the A, T, C, G, and U nucleotides.

These primers or probes can be composed totally or partially of alpha or beta anomerism nucleosides or isomers in the D or L series, or PNA (Nielsen et al., Nucleic Acid Research, 21(2), pp. 197–200, 1993).

In another embodiment of the invention, the mutation or mutations is/are detected by sequencing all or part of the protease gene.

The various sequencing methods are well known: In particular, the sequencing methods of Sanger, the sequencing methods using four wells to react the sequences studied with sequencing primers labeled by four different fluorophores (Perkin-Elmer "ABI Prism Dye Primer" procedure), or the method described in U.S. Pat. No. 5,795,722 (Visible Genetics), or the method using labeled nucleotides (Perkin-Elmer "ABI Prism Dye Terminator" procedure) instead of labeled primers can be used. The sequencing methods are described, for example, in Molecular Cloning, A Laboratory Manual, Sambrook, Fritsch, and Maniatis, Cold Spring Harbor Laboratory Press, 1989, Chapter 13.

In a particular embodiment of the invention, the presence of only one or more given mutations is tested. In another embodiment of the invention, both the mutated nucleotide sequence and the wild-type (non-mutated) nucleotide sequence are tested. If a hybridization method is used, at least two types of probes are defined for each position able to mutate: a probe type specific to the mutated sequence and a probe type specific to the wild-type sequence. Using both these types of probes enables the method to be controlled, since at least one of the two probe types has to react. Another advantage is to reveal the presence of mutated strains and wild-type strains in a given patient, where present.

Preferably, the target nucleic acid is subjected to a preliminary enzymatic amplification reaction to increase the sensitivity of the test, but it is possible to detect the target nucleic acid directly. The articles by Lewis (1992, Genetic Engineering News, 12, 1–9), and Abramson and Myers (1993, Curr. Opin. Biotechnol., 4, 41–47) give examples of target amplification. The enzymatic amplification technique is, for example, chosen from the NASBA (Nucleic Acid Sequence Based Amplification), TMA (Transcription Mediated Amplification), RT-PCR (Reverse Transcriptase-Polymerase Chain Reaction), SDA (Strand Displacement Amplification), or LCR (Ligase Chain Reaction) techniques.

Mutant viral strains are detected from a possibly pretreated biologic sample. "Pretreatment" means the various steps by which the sample is treated to make the target nucleic.acid, namely the protease gene, accessible, for example lysis, fluidization, concentration, or capture (see for example U.S. Pat. Nos. 5,750,388 and 5,766,849) using methods known of themselves.

To extract the viral RNA, one may, for example, use the reagent sold by the Boeringher Mannheim Company (High Pure Viral RNA reference 1858882) or the Quiagen kit (Viral RNA reference 29504). Other procedures are described in Maniatis et al., Molecular Cloning: A Laboratory Manual, 2nd Edition, Cold Spring Harbor Laboratory Press, 1989. The biologic sample can be any sample from the human body or possibly a sample enriched by culturing, such as blood, sperm, skin tissue, bronchoalveolar lavage fluid, biopsy, urine, colonies, liquid culture, etc.

The following examples illustrate the invention.

EXAMPLES

Example 1

A study was conducted on three patients infected with HIV-2. Patients 1 and 2 had never received antiproteases. Patient 3 had already received Ritonavir for 8 months, and this treatment had been withdrawn 5 months before the study started. The first sample studied was taken before the beginning of treatment in patients 1 and 2, and 6 weeks after the start of Ritonavir treatment for patient 3. In patients 1 and 2, samples taken 2 and 5 months respectively after the start of treatment were studied. For patient 3, two samples (8 months and 11 months) were analyzed. Treatment consisted of Ritonavir for patient 2 and Ritonavir/Saquinavir for patients 1 and 3, at the recommended doses.

Methods:

The plasmas were obtained by centrifuging whole blood at 800 g for 10 minutes and clarified by a second centrifugation at 3000 g for 15 minutes.

500 microliters of pure plasma were added to 1.5 milliliters of fresh lymphocyte culture stimulated by PHA ($10^6$ cells/dish). Viral replication in the supernatant was monitored twice a week by measuring the level of HIV P-24 antigen (ELAVIA Ag I, Sanofi Diagnostics Pasteur). The positive supernatants were stored at −80° C. After ultracentrifugation of 1 milliliter of supernatant (23,500 g for 1 hour), the HIV-2 RNA was extracted by means of the Amplicor HCV Specimen Preparation kit (Roche).

The protease gene was retrotranscribed from 10 microliters of viral RNA solution and amplified with the Titan One Tube RT-PCR kit (Roche Molecular Diagnostics). Reverse transcription and the first amplification were done with the 3' Prot and 5' RT 3 primers (see below). The reaction at 50° C. for 30 minutes was followed by a denaturing step at 94° C. for 5 minutes then 40 cycles (30 seconds at 94° C., 30 seconds at 55° C., 90 seconds at 68° C.), and finally at 68° C. for 7 minutes. The step PCR stage was done with 5 microliters of the product of the first stage with primers 3' RTD and 5' Prot 2.1, with 5 minutes denaturing at 94° C., followed by 30 cycles (30 seconds at 94° C., followed by 30 cycles at 55° C., and 30 seconds at 72° C.) and finally 10 minutes at 72° C. The primer sequence is the following:

3' Prot: CAGGGGCTGACACCAACAGCACCCCC (SEQ ID NO: 1)

5' RT 3: CCATTTTTTCACAGATCTCTTTTAATGC-CTC (SEQ ID NO: 2)

3' RTD: ATGTGGGGGTATTATAAGGATTT (SEQ ID NO: 3)

5' Prot 2.1: GAAAGAAGCCCCGCAACTTC (SEQ ID NO: 4)

The amplification products were purified with the QUI-ACQUICK PCR purification kit (Quiagen) and sequenced directly with the 3' RTD and 5' Prot 2.1 primers using the ABI Prism Dye Terminator Cycle Sequencing kit (Applied Biosystem). They were analyzed with the Applied Biosystem 377 automatic sequencer and the sequences were aligned with the HIV-2 consensus sequences (subtypes A and B).

Results:

Before treatment, no mutation was detected relative to the HIV-2 A and B consensus sequences.

After treatment, the following mutations were observed:

position 45: In patients 1 and 2, coexistence of a non-mutated population (lysine; codon AAA) and a mutated population (arginine; codon AGA) were observed, namely the K45K/R mutation was observed;

position 54: In patients 1 and 2, replacement of isoleucine (codon ATA) by methionine (codon ATG), namely the I54M mutation, was observed;

position 64: A non-mutated population was observed, and a population in which isoleucine (codon ATA) was replaced by a valine (codon GTA), namely mutation I64I/V;

position 84: In patient 3, a non-mutated population (isoleucine (codon ATC) and a mutated population with replacement of isoleucine by a leucine (codon CTC) were observed, namely the I84I/L mutation;

position 90: In all 3 patients, replacement of leucine (codon CTG) by a methionine (codon ATG) was observed, namely the L90M mutation.

Similarly, the following mutations were observed:

position 10: Replacement of valine (codon GTA) by an isoleucine (codon ATA): i.e. mutation V10I when a patient was treated with Ritonavir;

position 46: Replacement of isoleucine (codon ATA) by a valine (codon GTA): i.e. mutation I46V when a patient was treated with Ritonavir; and position 82: Replacement of isoleucine (codon ATA) by a methionine (codon ATG): i.e. mutation I82M when a patient was treated with Indinavir.

Example 2

Example of Probes that can be used for Detecting Mutations on the HIV-2 Protease Gene The probes usable for revealing any mutations according to the invention, using hybridization techniques, can be defined from alignments published by Myers G. et al., 1997, Human Retroviruses and AIDS: A compilation and analysis of nucleic acid and amino acid sequences, Los Alamos National Laboratory, Los Alamos, N.Mex.

Of course, in addition to the probes expressly defined below, the invention also includes equivalent nucleotide probes, namely probes able to detect the same mutations on the protein sequence of the protease as those detected by the probes defined below, taking into account degeneration in the genetic code, namely the fact that a given amino acid can be coded by different codons.

Thus, the expression "equivalent nucleotide sequences" means any nucleotide sequences that differ from each other by at least one nucleotide but whose translation leads to the same protein sequence, in other words all nucleotide sequences coding for the same protein sequence.

Of course, this comment applies to each codon in each probe. Thus, for example, the amino acid in position 53 of HIV-2 protease is a phenylalanine which can be coded either by codon TTT or by codon TTC. The probes corresponding to each of these possibilities are of course part of the invention.

Depending on the particular hybridization conditions, particularly the temperature and composition of the hybridization and washing buffers, it is possible to define probes that must include at least one of the minimum sequences below, or their complementary sequences. Probes containing these sequences enable mutations to be distinguished in a hybridization process. Of course, analogous probes, obtained in particular by introducing base analogs such as inosine or nebularin in positions where polymorphism due to intrinsic variability of the virus is present lead to a similar result and are also part of the invention.

These sequences are given in the 5' to 3' direction:

CCA AAA ATA for a wild-type form of position 45.
CCA AAA GTA for a wild-type form of position 45.
CCT AAA ATA for a wild-type form of position 45.
CCA AGA ATA for a mutated form of position 45.
CCA AGA GTA for a mutated form of position 45.
CCT AGA ATA for a mutated form of position 45.
TTT ATA AAC for a wild-type form of position 54.
TTT ATA AAT for a wild-type form of position 54.
TTT ATG AAC for a mutated form of position 54.
TTT ATG AAT for a mutated form of position 54.
GAA ATA AAA for a wild-type form of position 64.
GAA ATA GAA for a wild-type form of position 64.
GAA GTA AAA for a mutated form of position 64.
GAA GTA GAA for a mutated form of position 64.
AAC ATC TTT for a wild-type form of position 84.
AAC ATT TTT for a wild-type form of position 84.
AAC CTC TTT for a mutated form of position 84.
ATT CTG ACA for a wild-type form of position 90.
ATC CTG ACA for a wild-type form of position 90.
ATT CTA ACA for a wild-type form of position 90.
ATC CTA ACA for a wild-type form of position 90.
ATT ATG ACA for a mutated form of position 90.
ATC ATG ACA for a mutated form of position 90.
or:
CCA GTA GTC for a wild-type form of position 10.
CCA ATA GTC for a mutated form of position 10.
AAA ATA GTA for a wild-type form of position 46.
AAA GTA GTA for a mutated form of position 46.

CCA ATC AAC for a wild-type form of position 82.
CCA ATA AAC for a wild-type form of position 82.
CCA ATG AAC for a mutated form of position 82.

To obtain probes longer than those with the minimum sequences of 9 nucleotides shown above, it is of course necessary to choose additional nucleotides in order to respect the sequence of the adjacent regions on either side of the minimum sequence in the gene of the protease of an HIV-2 strain. These sequences can be obtained from databases.

For example, the probes indicated below, or their complementary probes, can be used.

(a) position 45:

A probe having for example 9 to 25 nucleotides (preferably distributed symmetrically about the mutated codon AGA) whose sequence is included in one of the following sequences:

ATTACACTCCAAGAATAGTAGGGGG (SEQ ID NO: 5)

ATTATAGCCCAAGAATAGTAGGGGG (SEQ ID NO: 6)

ATTATAGTCCAAGAATAGTAGGGGG (SEQ ID NO: 7)

ATTATACCCCAAGAATAGTAGGGGG (SEQ ID NO: 8)

ATTATAGTCCAAGAATAGTAGGAGG (SEQ ID NO: 9)

ATTATACCCCAAGAATAGTAGGAGG (SEQ ID NO: 10) can be used.

(b) position 54:

A probe having for example 9 to 25 nucleotides (preferably distributed symmetrically about the mutated codon ATG) whose sequence is included in one of the following sequences:

TAGGGGGATTTATGAACACCAAAGA (SEQ ID NO: 11)

TAGGGGGATTCATGAACACCAAAGA (SEQ ID NO: 12)

TAGGAGGATTCATGAACACCAAAGA (SEQ ID NO: 13)

TAGGAGGGTTCATGAACACCAAAGA (SEQ ID NO: 14) can be used.

(c) position 64:

A probe having for example 9 to 25 nucleotides preferably distributed symmetrically about the mutated codon GTA) whose sequence is included in one of the following sequences:

AAAATGTAGAAGTAAAAGTACTAAA (SEQ ID NO: 15)

AAAATATAGAAGTAAAAGTACTAAA (SEQ ID NO: 16)

AAGATGTAGAAGTAAAGGTACTAAA (SEQ ID NO: 17)

AAAATGTAGAAGTAGAAGTTCTAAA (SEQ ID NO: 18)

AAAATGTAGAAGTAGAAGTCCTGGA (SEQ ID NO: 19)

AAAGTGTAGAAGTAAGAGTGCTAAA (SEQ ID NO: 20) can be used.

(d) position 84:

A probe having for example 9 to 25 nucleotides (preferably distributed symmetrically about the mutated codon CTC) whose sequence is included in one of the following sequences:

CCCCAATCAACCTCTTTGGCAGAAA (SEQ ID NO: 21) can be used.

(e) position 90:

A probe having for example 9 to 25 nucleotides (preferably distributed symmetrically about the mutated codon ATG) whose sequence is included in one of the following sequences:

GCAGAAATATTATGACAGCCTTAGG (SEQ ID NO: 22)

GCAGAAATATTATGGCAACCTTAGG (SEQ ID NO: 23)

GCAGAAATGTTATGACAGCTTTAGG (SEQ ID NO: 24)

GCAGAAATATCATGACAGCCTTGGG (SEQ ID NO: 25)

GCAGAAACATTATGACAGCCTTA (SEQ ID NO: 26) can be used.

What is claimed is:

1. Method for testing, in a biological sample from a patient infected by HIV-2 containing at least one HIV-2 viral strain, the resistance of said HIV-2 viral strain to treatment with an antiprotease agent, comprising investigating the presence of a mutation at positions 90 of the protein sequence of the protease of said viral strain, said mutation having previously been found to elicit said resistance, and if such a mutation is found, concluding that a viral strain resistant to said antiprotease agent is present in the patient in question.

2. Method according to claim 1, wherein:
   a) the presence of a mutation at position 90 of the protein sequence of the protease of said viral strain in a biological sample taken from a patient infected with HIV-2 is investigated,
   b) a mutation found in a) which, after cloning in an HIV-2 virus, does not prevent the virus clone obtained from multiplying in culture in the presence of said antiprotease drug is selected, and
   c) if the mutation is selected at step b), it is concluded that resistance exists to the antiprotease drug referred to in b).

3. Method according to claim 1, wherein the presence of the mutation L90M, in the protein sequence of the protease of said viral strain is investigated and in which said resistance is concluded to exist if said mutation is present.

4. Method according to claim 1, wherein, to detect a mutation of the protein sequence of the protease, a corresponding mutation is sought in the nucleotide sequence of the gene of said protease.

5. Method according to claim 4, wherein said test is carried out using hybridization techniques.

6. Method according to claim 4, wherein said test is carried out using sequencing techniques.

7. The method of claim 4, wherein said mutation in the sequence of the gene corresponds to L90M.

8. The method of claim 7, wherein said mutation corresponds to a codon for position 90, which is ATG, instead of CTG or CTA.

9. The method of claim 1, said method further comprising investigating the presence of at least one additional mutation at one or more of positions 10, 45, 46, 54, 64, 82 and 84 of the protein sequence of the protease of said viral strain.

10. The method of claim 9, wherein the at least one additional mutation is selected from the following mutations: V10I, K45R, I46V, I54M, I64V, I82M and I84L.

11. The method of claim 9, wherein, to detect the at least one additional mutation of the protein sequence of the protease, at least one corresponding mutation is sought in the nucleotide sequence of the gene of said protease.

12. The method of claim 9, wherein said additional mutation is at said position 10.

13. The method of claim 9, wherein said additional mutation is at said position 45.

14. The method of claim 9, wherein said additional mutation is at said position 46.

15. The method of claim 9, wherein said additional mutation is at said position 54.

16. The method of claim 9, wherein said additional mutation is at said position 64.

17. The method of claim 9, wherein said additional mutation is at said position 82.

18. The method of claim 9, wherein said additional mutation is at said position 84.

19. The method of claim 11, wherein said additional mutation corresponds to a codon for position 45, which is AGA, instead of AAA.

20. The method of claim 11, wherein said additional mutation corresponds to a codon for position 54, which is ATG, instead of ATA.

21. The method of claim 11, wherein said additional mutation corresponds to a codon for position 64, which is GTA, instead of ATA.

22. The method of claim 11, wherein said additional mutation corresponds to a codon for position 84, which is CTC, instead of ATC or ATT.

* * * * *

SEQUENCE LISTING

<160> NUMBER OF SEQ ID NOS: 26

<210> SEQ ID NO 1
<211> LENGTH: 26
<212> TYPE: DNA
<213> ORGANISM: Artificial Sequence
<220> FEATURE:
<223> OTHER INFORMATION: 3' Prot primer

<400> SEQUENCE: 1 cagggctga caccaacagc accccc          26

<210> SEQ ID NO 2
<211> LENGTH: 31
<212> TYPE: DNA
<213> ORGANISM: Artificial Sequence
<220> FEATURE:

-continued

```
<223> OTHER INFORMATION: 5' RT primer

<400> SEQUENCE: 2 ccatttttc acagatctct tttaatgcct c                                31

<210> SEQ ID NO 3
<211> LENGTH: 23
<212> TYPE: DNA
<213> ORGANISM: Artificial Sequence
<220> FEATURE:
<223> OTHER INFORMATION: 3' RTD primer

<400> SEQUENCE: 3 atgtggggt attataagga ttt                                         23

<210> SEQ ID NO 4
<211> LENGTH: 20
<212> TYPE: DNA
<213> ORGANISM: Artificial Sequence
<220> FEATURE:
<223> OTHER INFORMATION: 5' Prot 2.1 primer

<400> SEQUENCE: 4
gaaagaagcc ccgcaacttc                                            20

<210> SEQ ID NO 5
<211> LENGTH: 25
<212> TYPE: DNA
<213> ORGANISM: Artificial Sequence
<220> FEATURE:
<223> OTHER INFORMATION: Probe (position 45)

<400> SEQUENCE: 5
attacactcc aagaatagta ggggg                                      25

<210> SEQ ID NO 6
<211> LENGTH: 25
<212> TYPE: DNA
<213> ORGANISM: Artificial Sequence
<220> FEATURE:
<223> OTHER INFORMATION: Probe (position 45)

<400> SEQUENCE: 6
attatagccc aagaatagta ggggg                                      25

<210> SEQ ID NO 7
<211> LENGTH: 25
<212> TYPE: DNA
<213> ORGANISM: Artificial Sequence
<220> FEATURE:
<223> OTHER INFORMATION: Probe (position 45)

<400> SEQUENCE: 7
attatagtcc aagaatagta ggggg                                      25

<210> SEQ ID NO 8
<211> LENGTH: 25
<212> TYPE: DNA
<213> ORGANISM: Artificial Sequence
<220> FEATURE:
<223> OTHER INFORMATION: Probe (position 45)

<400> SEQUENCE: 8 attataccc aagaatagta ggggg                                       25
```

```
<210> SEQ ID NO 9
<211> LENGTH: 25
<212> TYPE: DNA
<213> ORGANISM: Artificial Sequence
<220> FEATURE:
<223> OTHER INFORMATION: Probe (position 45)

<400> SEQUENCE: 9
attatagtcc aagaatagta ggagg                                 25

<210> SEQ ID NO 10
<211> LENGTH: 25
<212> TYPE: DNA
<213> ORGANISM: Artificial Sequence
<220> FEATURE:
<223> OTHER INFORMATION: Probe (position 45)

<400> SEQUENCE: 10 attataccccc aagaatagta ggagg                                25

<210> SEQ ID NO 11
<211> LENGTH: 25
<212> TYPE: DNA
<213> ORGANISM: Artificial Sequence
<220> FEATURE:
<223> OTHER INFORMATION: Probe (position 54)

<400> SEQUENCE: 11 taggggatt tatgaacacc aaaga                                  25

<210> SEQ ID NO 12
<211> LENGTH: 25
<212> TYPE: DNA
<213> ORGANISM: Artificial Sequence
<220> FEATURE:
<223> OTHER INFORMATION: Probe (position 54)

<400> SEQUENCE: 12 taggggatt catgaacacc aaaga                                  25

<210> SEQ ID NO 13
<211> LENGTH: 25
<212> TYPE: DNA
<213> ORGANISM: Artificial Sequence
<220> FEATURE:
<223> OTHER INFORMATION: Probe (position 54)

<400> SEQUENCE: 13
taggaggatt catgaacacc aaaga                                 25

<210> SEQ ID NO 14
<211> LENGTH: 25
<212> TYPE: DNA
<213> ORGANISM: Artificial Sequence
<220> FEATURE:
<223> OTHER INFORMATION: Probe (position 54)

<400> SEQUENCE: 14
taggagggtt catgaacacc aaaga                                 25

<210> SEQ ID NO 15
<211> LENGTH: 25
<212> TYPE: DNA
<213> ORGANISM: Artificial Sequence
<220> FEATURE:
<223> OTHER INFORMATION: Probe (position 64)
```

```
<400> SEQUENCE: 15
aaaatgtaga agtaaaagta ctaaa                                    25

<210> SEQ ID NO 16
<211> LENGTH: 25
<212> TYPE: DNA
<213> ORGANISM: Artificial Sequence
<220> FEATURE:
<223> OTHER INFORMATION: Probe (position 64)

<400> SEQUENCE: 16
aaaatataga agtaaaagta ctaaa                                    25

<210> SEQ ID NO 17
<211> LENGTH: 25
<212> TYPE: DNA
<213> ORGANISM: Artificial Sequence
<220> FEATURE:
<223> OTHER INFORMATION: Probe (position 64)

<400> SEQUENCE: 17
aagatgtaga agtaaaggta ctaaa                                    25

<210> SEQ ID NO 18
<211> LENGTH: 25
<212> TYPE: DNA
<213> ORGANISM: Artificial Sequence
<220> FEATURE:
<223> OTHER INFORMATION: Probe (position 64)

<400> SEQUENCE: 18
aaaatgtaga agtagaagtt ctaaa                                    25

<210> SEQ ID NO 19
<211> LENGTH: 25
<212> TYPE: DNA
<213> ORGANISM: Artificial Sequence
<220> FEATURE:
<223> OTHER INFORMATION: Probe (position 64)

<400> SEQUENCE: 19
aaaatgtaga agtagaagtc ctgga                                    25

<210> SEQ ID NO 20
<211> LENGTH: 25
<212> TYPE: DNA
<213> ORGANISM: Artificial Sequence
<220> FEATURE:
<223> OTHER INFORMATION: Probe (position 64)

<400> SEQUENCE: 20
aaagtgtaga agtaagagtg ctaaa                                    25

<210> SEQ ID NO 21
<211> LENGTH: 25
<212> TYPE: DNA
<213> ORGANISM: Artificial Sequence
<220> FEATURE:
<223> OTHER INFORMATION: Probe (position 84)

<400> SEQUENCE: 21
ccccaatcaa cctctttggc agaaa                                    25

<210> SEQ ID NO 22
<211> LENGTH: 25
```

```
<212> TYPE: DNA
<213> ORGANISM: Artificial Sequence
<220> FEATURE:
<223> OTHER INFORMATION: Probe (position 90)

<400> SEQUENCE: 22
gcagaaatat tatgacagcc ttagg                                         25

<210> SEQ ID NO 23
<211> LENGTH: 25
<212> TYPE: DNA
<213> ORGANISM: Artificial Sequence
<220> FEATURE:
<223> OTHER INFORMATION: Probe (position 90)

<400> SEQUENCE: 23
gcagaaatat tatggcaacc ttagg                                         25

<210> SEQ ID NO 24
<211> LENGTH: 25
<212> TYPE: DNA
<213> ORGANISM: Artificial Sequence
<220> FEATURE:
<223> OTHER INFORMATION: Probe (position 90)

<400> SEQUENCE: 24
gcagaaatgt tatgacagct ttagg                                         25

<210> SEQ ID NO 25
<211> LENGTH: 25
<212> TYPE: DNA
<213> ORGANISM: Artificial Sequence
<220> FEATURE:
<223> OTHER INFORMATION: Probe (position 90)

<400> SEQUENCE: 25
gcagaaatat catgacagcc ttggg                                         25

<210> SEQ ID NO 26
<211> LENGTH: 23
<212> TYPE: DNA
<213> ORGANISM: Artificial Sequence
<220> FEATURE:
<223> OTHER INFORMATION: Probe (position 90)

<400> SEQUENCE: 26
gcagaaacat tatgacagcc tta                                           23
```